US011040152B2

(12) United States Patent
Kim et al.

(10) Patent No.: US 11,040,152 B2
(45) Date of Patent: Jun. 22, 2021

(54) INJECTION DEVICE AND METHODS RELATED THERETO

(71) Applicants: Southern Research Institute, Birmingham, AL (US); UAB Research Foundation, Birmingham, AL (US)

(72) Inventors: Harrison Kim, Birmingham, AL (US); Patrick Schexnailder, Birmingham, AL (US)

(73) Assignees: SOUTHERN RESEARCH INSTITUTE, Birmingham, AL (US); THE UAB RESEARCH FOUNDATION, Birmingham, AL (US)

( * ) Notice: Subject to any disclaimer, the term of this patent is extended or adjusted under 35 U.S.C. 154(b) by 380 days.

(21) Appl. No.: 15/760,164

(22) PCT Filed: Sep. 14, 2016

(86) PCT No.: PCT/US2016/051619
§ 371 (c)(1),
(2) Date: Mar. 14, 2018

(87) PCT Pub. No.: WO2017/048772
PCT Pub. Date: Mar. 23, 2017

(65) Prior Publication Data
US 2018/0264202 A1    Sep. 20, 2018

Related U.S. Application Data

(60) Provisional application No. 62/220,435, filed on Sep. 18, 2015.

(51) Int. Cl.
*A61M 5/32* (2006.01)
*A61D 7/00* (2006.01)
*A61D 3/00* (2006.01)

(52) U.S. Cl.
CPC ............. *A61M 5/3287* (2013.01); *A61D 3/00* (2013.01); *A61D 7/00* (2013.01); *A61M 5/3271* (2013.01); *A61M 5/3202* (2013.01)

(58) Field of Classification Search
CPC .. A61M 5/3287; A61M 5/3271; A61M 5/428; A61B 17/3403; A61D 3/00; A61D 7/00
See application file for complete search history.

(56) References Cited

U.S. PATENT DOCUMENTS

| 4,497,325 A | 2/1985 | Wedel |
| 4,515,590 A * | 5/1985 | Daniel .................. A61D 1/025 |
| | | 604/144 |

(Continued)

FOREIGN PATENT DOCUMENTS

| WO | WO-2008/140303 A1 | 11/2008 | |
| WO | WO-2008140303 A1 * | 11/2008 | ........ E04F 15/02494 |

OTHER PUBLICATIONS

International Search Report and Written Opinion dated Jan. 26, 2017 by the International Searching Authority for Patent Application No. PCT/US2016/051619, which was filed on Sep. 14, 2016 and published as WO 2017/048772 on Mar. 23, 2017 (Inventor—Kim et al.; Applicants—Southern Research Foundation et al.) (9 pages).

*Primary Examiner* — Nathan R Price
*Assistant Examiner* — Courtney B Frederickson
(74) *Attorney, Agent, or Firm* — Ballard Spahr LLP

(57) ABSTRACT

Disclosed herein is an injection device with housing that defines a channel and a first injection guide opening. The first injection guide opening enters the channel in a manner that allows a needle to penetrate a vessel in an animal with accuracy and at the same time protect the user from the needle.

18 Claims, 18 Drawing Sheets

(56) References Cited

U.S. PATENT DOCUMENTS

| | | | | |
|---|---|---|---|---|
| 4,585,436 A | * | 4/1986 | Davis | A61M 1/1643 |
| | | | | 604/29 |
| 2004/0133111 A1 | * | 7/2004 | Szczech | A61B 8/0833 |
| | | | | 600/461 |
| 2005/0182369 A1 | | 8/2005 | Miller | |
| 2010/0324466 A1 | * | 12/2010 | Chau | A61M 1/367 |
| | | | | 604/6.16 |
| 2013/0253416 A1 | * | 9/2013 | Rotenstreich | A61F 9/0017 |
| | | | | 604/22 |
| 2015/0157787 A1 | | 6/2015 | Cully et al. | |

* cited by examiner

INJECTION DEVICE AND METHODS RELATED THERETO

CROSS-REFERENCE TO RELATED APPLICATIONS

This application is a U.S. National Phase Application of PCT/US2016/051619, filed on Sep. 14, 2016, which claims the benefit of U.S. Provisional Application No. 62/220,435, filed on Sep. 18, 2015, each of which are incorporated herein by reference in their entirety.

BACKGROUND

Vascular access in animals is a common procedure and can be an occupational hazard for individuals working with the animals. There is typically no barrier between the needle and an individual's hand, and movement (of either the individual and/or the animal) may result in a percutaneous needle stick.

Accordingly, there is a need in the art for devices and methods that provide protection to an individual simultaneously handling a needle and an animal. Such a device and method are disclosed herein.

SUMMARY

Described herein is an injection device comprising a) a housing defining a channel and a first injection guide opening, the channel having a central axis, the first injection guide opening surrounding a first injection axis, wherein the housing comprises i) first and second end surfaces that are spaced apart relative to a first housing axis; ii) a base surface extending between the first and second end surfaces; and iii) at least one upper surface extending between the first and second end surfaces, wherein the base surface and the at least one upper surface are spaced apart relative to a second housing axis that is perpendicular to the first housing axis; wherein the channel of the housing extends from the first end surface to the base surface, wherein the first injection guide opening is positioned in fluid communication with the channel, and wherein the first injection axis is substantially parallel to the first housing axis or the second housing axis. Methods of using the injection device are also disclosed. An exemplary method comprises a) providing the injection device disclosed herein; b) placing a body portion of an animal in the channel; and c) administering a substance to or withdrawing a fluid from a vessel in the body portion of the animal via a needle placed through the first injection guide opening.

Also disclosed herein is an injection device comprising a) an injection plate having first and second end portions that are spaced apart relative to a first axis the first and second end portions defining respective first and second side surfaces of the injection plate, wherein the injection plate has third and fourth side surfaces that extend between the first and second side surfaces relative to the first axis and are spaced apart relative to a second axis that is perpendicular to the first axis, and wherein the injection plate has an outer surface and an opposing inner surface that extend between the first, second, third, and fourth side surfaces of the injection plate, wherein the first and second end portions of the injection plate have respective concave inward curvatures relative to the second axis, and wherein the concave inward curvatures of the first and second end portions are substantially complementary to a shape of a human finger, wherein at least a portion of the upper surface is configured to receive and support at least a portion of an ear of an animal, wherein the distance between the first side surface and the second surface relative to the first axis is from about 2 cm to about 10 cm, and wherein the distance between the third side surface and the fourth side surface relative to the second axis is from about 3 cm to about 7 cm. Methods of using the injection device are also disclosed. An exemplary method comprises a) providing the injection device disclosed herein comprising an injection plate; b) placing at least one finger between the first and second end and against the inner surface of the injection plate; c) placing a body portion of an animal on the outer surface of the injection plate; and c) administering a substance to or withdrawing a fluid from a vessel in the animal.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

DETAILED DESCRIPTION

Figure 1:
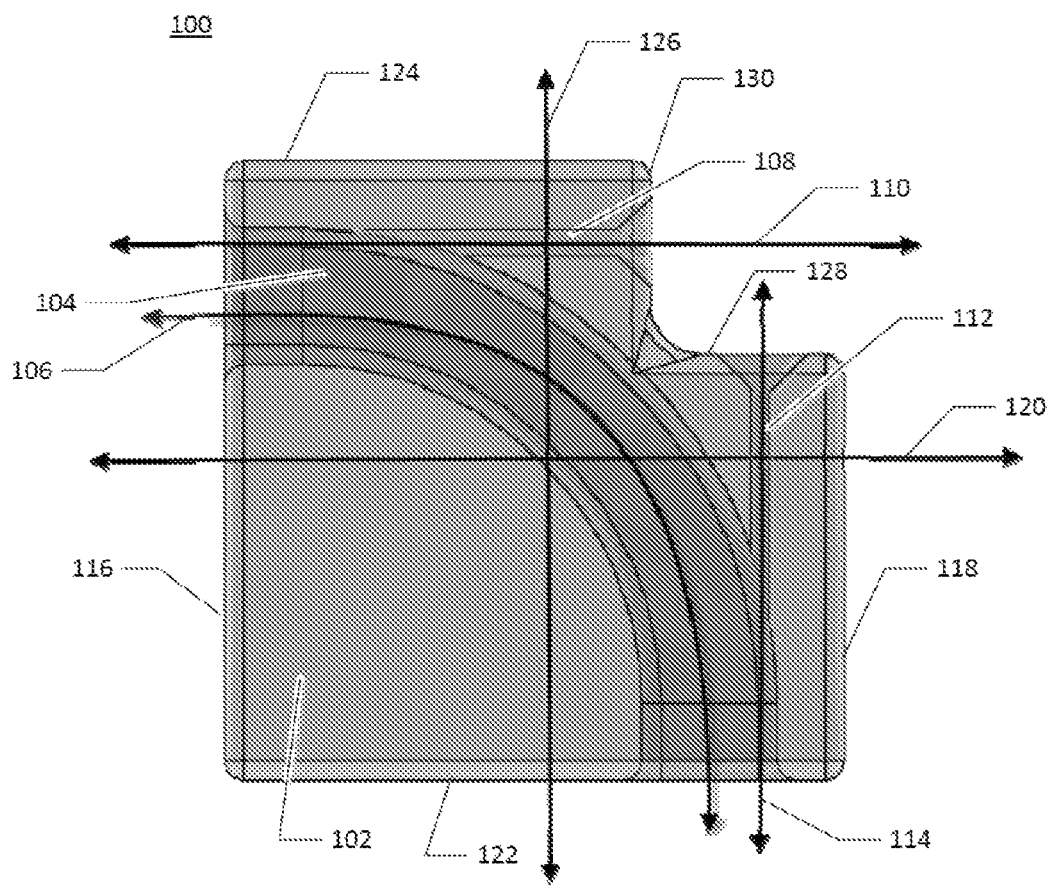
FIG. 1 shows a sectional view of an exemplary injection device as disclosed herein.
Figure 2:
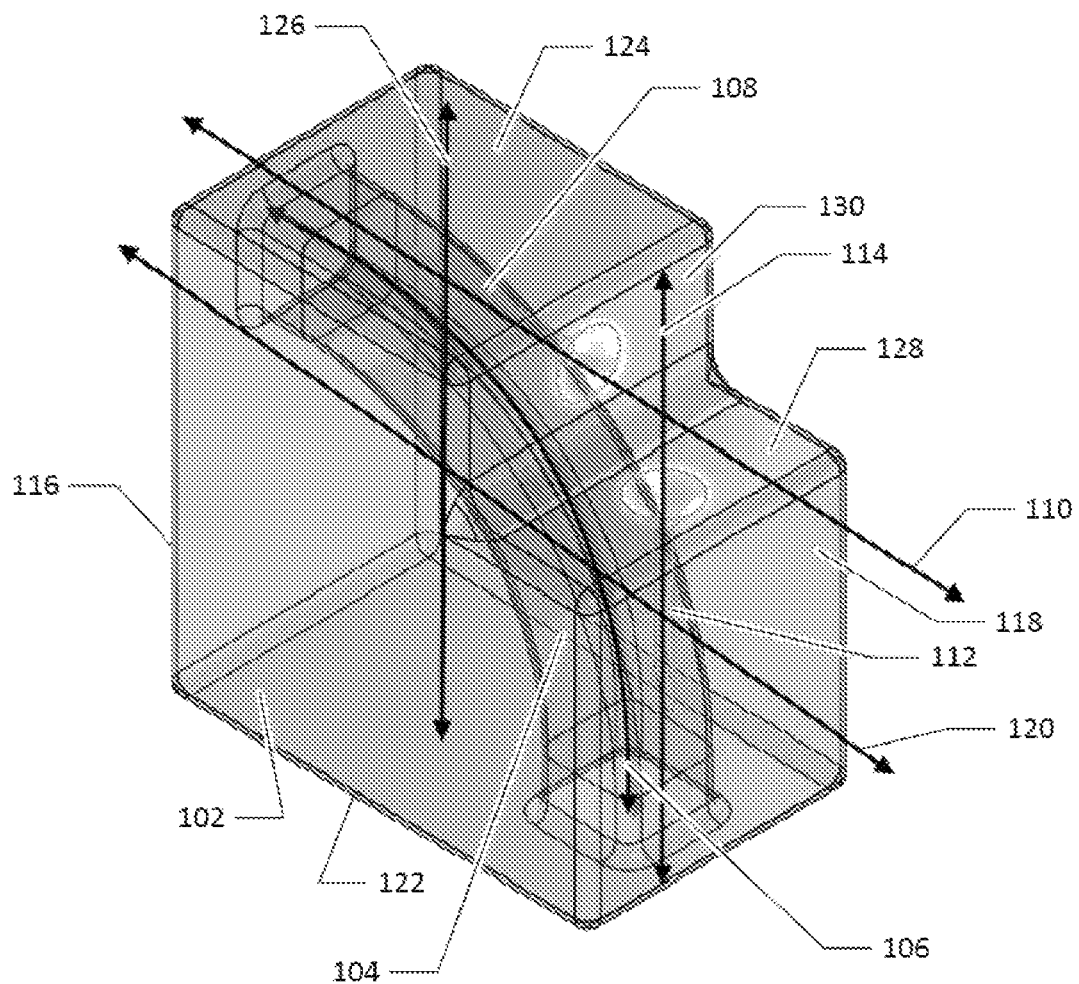
FIG. 2 shows a partially transparent isometric view of an exemplary injection device as disclosed herein.
Figure 3:
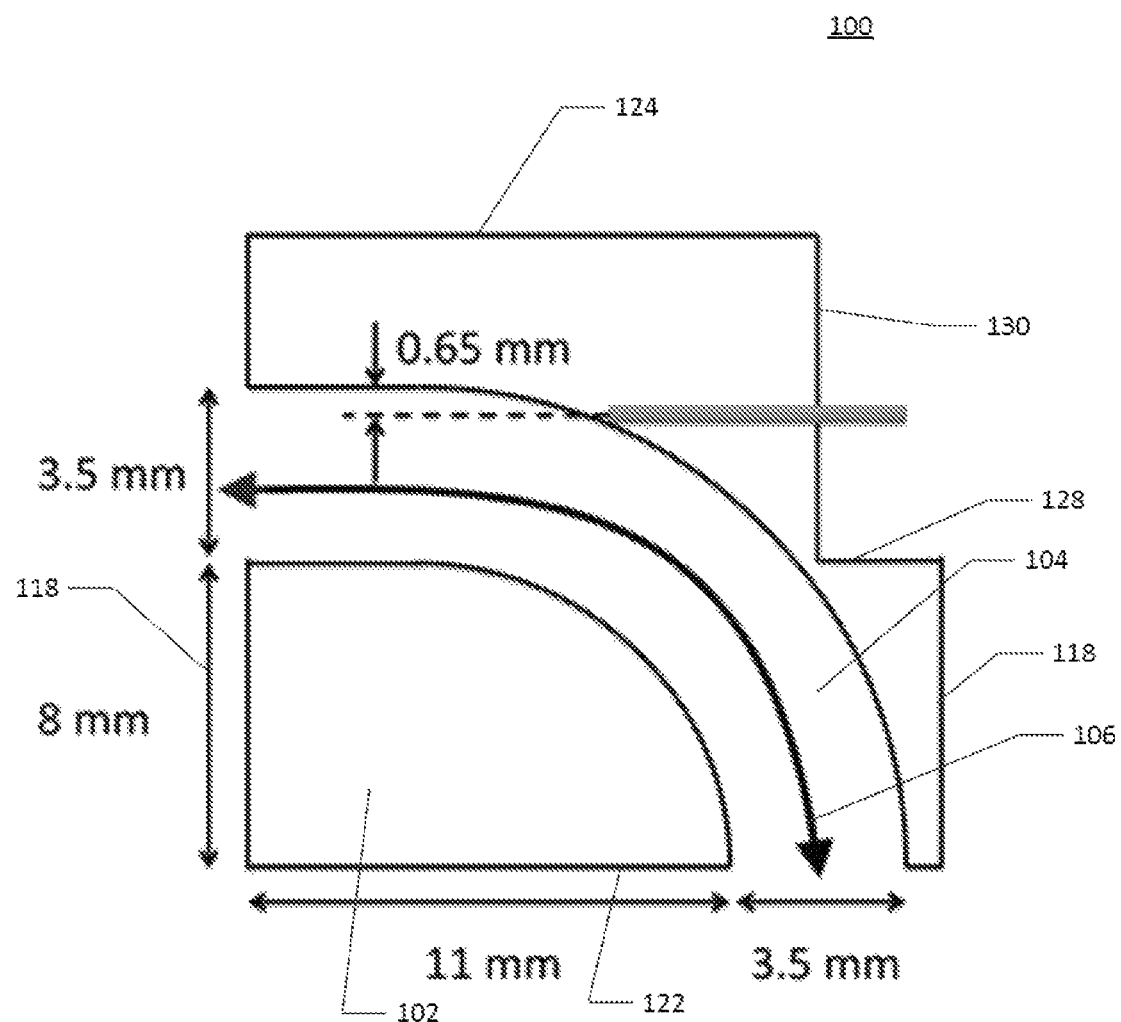
FIG. 3 shows a sectional view of an exemplary injection device as disclosed herein.
Figure 4:
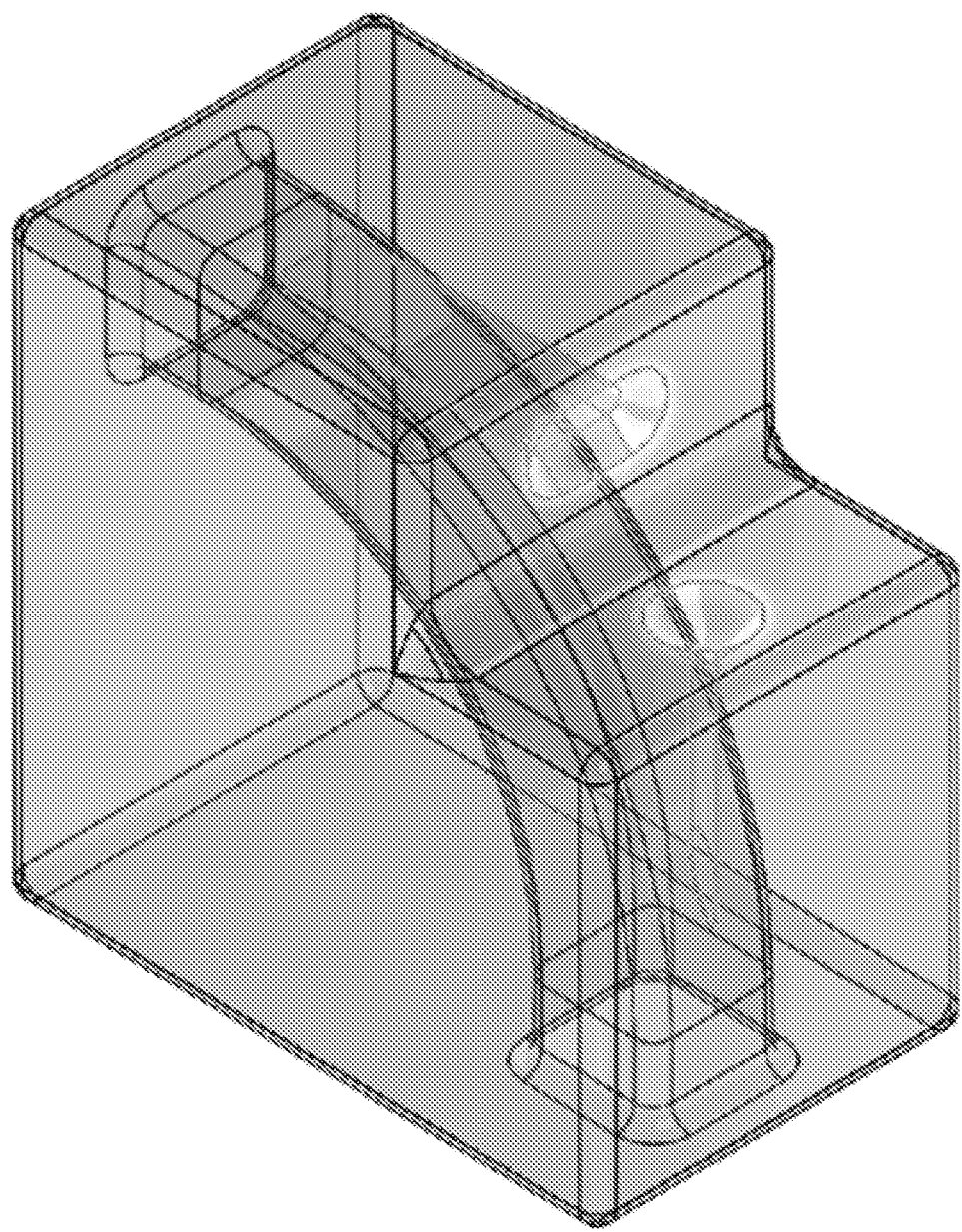
FIG. 4 shows a partially transparent isometric view of an exemplary injection device as disclosed herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

It is also to be understood that the terminology used herein is for the purpose of describing particular aspects only and is not intended to be limiting. Although any devices and methods similar or equivalent to those described herein can be used in the practice or testing of the present invention, example methods and materials are now described.

As used in the specification and in the claims, the term "comprising" can include the aspects "consisting of" and "consisting essentially of" Unless defined otherwise, all technical and scientific terms used herein have the same meaning as commonly understood by one of ordinary skill in the art to which this invention belongs. In this specification and in the claims, which follow, reference will be made to a number of terms which shall be defined herein.

As used in the specification and the appended claims, the singular forms "a," "an" and "the" include plural referents unless the context clearly dictates otherwise. Thus, for example, reference to "a subject" includes two or more subjects.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

1. INJECTION DEVICE

Injecting or withdrawing a substance via vascular access in a body portion, such as, for example, a tail or an ear, of an animal, such as, for example, a rat, mouse, rabbit, or pig, is a common procedure. However, this procedure is often an occupational hazard for individuals working with the animals. In a typical setting for handling rabbits, one individual restrains the animal and occludes a vessel, such as the marginal ear vein, proximal to the needle access point. Meanwhile, a second individual inserts a needle into the vessel, just distal to where the first individual is occluding the vessel. There is typically no barrier between the needle and the first individual's hand, and movement (of either individual and/or the animal) can result in a percutaneous needle stick.

In another typical setting for handling a rat or mouse, one individual restrains the animal and holds the tail of the animal while simultaneously inserting a needle into the vessel in the tail. There is also typically no barrier between the needle and the individual's hand, and movement (of either individual and/or the animal) can result in a percutaneous needle stick.

Accordingly, there is a need for an injection device that protects the individual while the individual simultaneously handles both an animal and a syringe with a needle for injection or withdrawal of a substance. There is also a need for an injection device that allows for penetration accuracy during the procedure.

Disclosed herein is an injection device that assists and protects an individual while the individual simultaneously handles both an animal and a syringe with a needle for injection or withdrawal of a substance.

Disclosed herein, in various aspects and with reference to FIGS. 1-5 and 7-13 is an injection device 100, 200 for positioning a body portion of an animal into a channel 104, 204. The injection device 100, 200 comprises a first injection guide opening 108, 208 that can assist a needle from entering the channel 104, 204 where the vessel of the body portion of the animal is located. As such, at least a portion of the needle is located within the injection device 100, 200 during use, and the individual handling the animal and/or needle can be shielded from the needle to eliminate or limit the risk of an accidental stick.

In one aspect, and with reference to FIGS. 1-5, the injection device 100 comprises a housing 102. The housing 102 defines a channel 104 and at least one injection guide opening 108, 112. The channel 104 has a central axis 106 that is centrally positioned within the channel. The injection guide opening 108 surrounds an injection axis 110. The housing 102 comprises first and second end surfaces 116, 118 that are spaced apart relative to a first housing axis 120. The housing 102 also comprises a base surface 122 extending between the first and second end surfaces 116, 118, and at least one upper surface 124, 128, and 130 extending between the first and second end surfaces 116, 118. The base surface 122 and the at least one upper surface 124, 128, and 130 can be spaced apart relative to a second housing axis 126 that is perpendicular to the first housing axis 120. The channel 104 of the housing 102 extends from the first end surface 116 to the base surface 122. The injection guide opening 108 is positioned in fluid communication with the channel 104, and the injection axis 110 can be substantially parallel to the first housing axis 120. Alternatively, in various aspects, instead of injection guide opening 108, the housing 102 can define injection guide opening 112, which surrounds injection axis 114. In these aspects, the guide opening 112 can be positioned in fluid communication with the channel 104, and the injection axis 114 can be substantially parallel to the second housing axis.

In an exemplary configuration, the housing 102 comprises a first injection guide opening 108 and a second injection guide opening 112, wherein the first injection guide opening 108 surrounds a first injection axis 110 and the second injection guide opening 112 surrounds a second injection axis 114. The first injection axis 110 is substantially parallel to the first housing axis 120 and the second injection axis 114 is substantially parallel to the second housing axis 126. Thus, in one aspect, the housing 102 further defines a second injection guide opening 112 that surrounds a second injection axis 114, wherein the second injection guide opening 112 is positioned in fluid communication with the channel 104, and wherein the second injection axis 114 is substantially parallel to the first housing axis 120 or the second housing axis 126.

In exemplary aspects, and with reference to FIGS. 1-4, the channel 104 can have an arcuate profile extending from the first end surface 116 to the base surface 122 of the housing. In these aspects, the central axis 106 of the channel 104 (and the surfaces of the housing defining the channel) can have a variable radius of curvature that varies between the first end surface 116 and the base surface 122. In exemplary aspects, the end portions of the central axis 106 proximate the first end surface 116 and the base surface 122 can have a greater radius of curvature than the intermediate portions of the central axis positioned between the end portions. As further disclosed herein and shown in FIG. 1, it is contemplated that within the end portions, the central axis 106 can be substantially parallel to the first or second injection axes 110, 114 or be angled relative to the first or second injection axes at a selected acute angle.

In one aspect, the first injection guide opening 108 extends from an upper surface 124, 128, and/or 130 of the at least one upper surface 124, 128, and/or 130 to the channel 104. Optionally, in this aspect, the first injection axis 110 is substantially parallel to the second housing axis 126.

In one aspect, the first injection guide 108 extends from the second end surface 118 to the channel 104. Optionally, in this aspect, the first injection axis 108 is substantially parallel to the first housing axis 120.

In one aspect, the first injection guide opening 108 extends from an upper surface 124, 128, or 130 of the at least one upper surface 124, 128, and/or 130 to the channel 104. and the second injection guide opening 112 extends from an upper surface of the at least one upper surface 124, 128, or 130 to the channel 104. Optionally, in this aspect, the first injection axis 110 is substantially parallel to the first housing axis 120, and the second injection axis 114 is substantially parallel to the second housing axis 126.

It is also understood that the first injection guide opening 108 can have an entry point from either the at least one upper surface 124, 128, and 130 or from the second end surface 118. As further disclosed herein, the housing 102 can define a first injection guide opening 108 and a second injection guide opening 112, wherein the first injection guide opening 108 and the second injection guide opening 112 have respective entry points defined in upper surfaces 128, 130.

In one aspect, a portion of the central axis 106 is substantially parallel to the first housing axis 120 and/or the first injection axis 110. For example, a portion of the central axis 106 can be substantially parallel to the first housing axis 120. In another example, a portion of the central axis 106 can be substantially parallel to the first injection axis 110. In yet another example, a portion of the central axis 106 can be substantially parallel to the first housing axis 120 and the first injection axis 110.

In one aspect, a portion of the central axis 106 can be substantially parallel to the second housing axis 126 and/or the second injection axis 114. For example, a portion of the central axis 106 can be substantially parallel to the second housing axis 126. In another example, a portion of the central axis 106 can be substantially parallel to the second injection axis 114. In yet another example, a portion of the central axis 106 can be substantially parallel to the second housing axis 126 and the second injection axis 114.

In one aspect, a first portion of the central axis 106 can be substantially parallel to the first housing axis 120 and/or the first injection axis 110, and a second portion of the central axis 106 can be substantially parallel to the second housing axis 126 and/or the second injection axis 114.

In one aspect, the housing 102 surrounds and encloses at least a portion of the channel 104 between the end openings of the channel. However, as further disclosed herein, the channel can be in communication with one or more openings that extend outwardly relative to the central axis of the channel, Thus, in some aspects, aside from the portions of the channel that connect to the first injection guide opening 108, the second injection guide opening 112, and/or other radially extending openings, the outer diameter of the channel can be defined by the housing. Similarly, it is contemplated that the housing 102 can surround and enclose at least a portion of the guide openings 108, 112 between the outer entrances to the guide openings and the channel 104.

In one aspect, the cross-sectional shape of the channel 104 can be any shape, such as, for example, square, rectangular, circular, oval, hexagonal, octagonal, pentagonal, or heptagonal. In one aspect, the diameter or width of the channel 104 can be uniform throughout the channel 104. In another aspect, the diameter or width of the channel 104 can be non-uniform. Optionally, the diameter or width of the channel can taper from one end to the other end. In one aspect, channel 104 has a width or diameter from about 2 mm to about 5 mm. For example, channel 104 can have a width or diameter from about 3 mm to about 4 mm.

In one aspect, channel 104 is configured to receive at least a portion of a body part of an animal, such as, for example, a portion of the tail of a rodent, such as, for example, a mouse or rat.

In one aspect, the first injection axis 110 and the central axis 106, when substantially parallel, are spaced apart in a manner so that a needle entering the channel 104 via the first injection guide opening 108 enters a vessel located in a body portion of an animal within the channel 104. For example, a vessel within a mouse tail is located some distance from the outside surface of the tail. As such, in one example, the first injection axis 110 and the central axis 106, when substantially parallel, can be spaced apart in a configuration so that a needle entering the channel 104 via the first injection guide opening 108 enters a vessel located in a tail of a mouse within the channel 104. As such, the needle is contained within the injection device during injection or withdrawal of a substance in/from the animal, and the individual performing the procedure is protected from the needle.

Thus, in one aspect, at least a portion of the central axis 106 that is substantially parallel to the first injection axis 110 is spaced apart from the first injection axis 110 relative to the first housing axis 120 at a distance from about 0.8 mm to about 1.4 mm. In one aspect, at least a portion of the central axis 106 that is substantially parallel to the first injection axis 110 is spaced apart from the first injection axis 110 relative to the first housing axis 120 at a distance from about 1.0 mm to about 1.2 mm. It is contemplated that such a distance can allow for a needle to enter the vessel in a mouse/rat tail positioned within the channel 104. An exemplary configuration of such positioning can be seen in FIGS. 3, 5A, and 5B.

In one aspect, at least a portion of the central axis 106 that is substantially parallel to the second injection axis 114 is spaced apart from the second injection axis 114 relative to the second housing axis 126 at a distance from about 0.8 mm to about 1.4 mm. In one aspect, at least a portion of the central axis 106 that is substantially parallel to the second injection axis 114 is spaced apart from the second injection axis 114 relative to the second housing axis 126 at a distance from about 1.0 mm to about 1.2 mm. It is contemplated that such a distance can allow for a needle to enter the vessel in a mouse/rat tail positioned within the channel 104.

In one aspect, the injection device 100 further comprises a first injection insert guide (not shown) that is at least partially received within the first injection guide opening 108. In this aspect, the first injection insert guide surrounds the first injection axis 108. In another aspect, the injection device 100 further comprises a second injection insert guide (not shown) that is at least partially received within the second injection guide opening 112. In this aspect, the second injection insert guide surrounds the second injection axis 114. The first and/or second injection insert guide can be made of a suitable material to guide a needle through the first injection guide opening 108. Non-limiting materials for the first and/or second injection insert guide include, plastic and metal.

In one aspect, and with reference to FIGS. 7-13, disclosed herein is another exemplary injection device 200, which can have any of the features or properties of injection device 100 as disclosed above. Thus, except where otherwise indicated, elements of the injection device 200 can have the same structure or function of corresponding elements of injection device 100.

In one aspect, the injection device 200 comprises a housing 202. The housing 202 defines a channel 204 and a first injection guide opening 208. The channel 204 has a central axis 206 that is centrally positioned within the channel. The first injection guide opening 208 surrounds a first injection axis 210. The housing 202 comprises first and second end surfaces 216, 218 that are spaced apart relative to a first housing axis 220. The housing 202 also comprises a base surface 222 extending between the first and second end surfaces 216, 218, and at least one upper surface 224 extending between the first and second end surfaces 216, 218, wherein the base surface 222 and the at least one upper surface 224 are spaced apart relative to a second housing axis 226 that is perpendicular to the first housing axis 220. The channel 204 of the housing 202 extends from the first end surface 216 to the base surface 222, and the first injection guide opening 208 is positioned in fluid communication with the channel 204. The first injection axis 210 can be substantially parallel to the first housing axis 220 or the second housing axis 226. The injection device 200 can also comprise a third housing axis 232, which is substantially parallel to both the first housing axis 220 and the second housing axis 226. It is understood that the first end surface 216 can be the second end surface 218, and vice versa.

In one aspect, the channel 204 in the injection device 200 can be configured to receive a portion of a body part of an animal, such as, for example, a portion of an ear of a rabbit or pig. In one aspect, the channel 204 in the injection device 200 is configured to receive an ear of a rabbit. In such an injection device, the first injection guide opening 208 can be positioned such that a needle entering the channel via the first injection guide opening 208 would enter a vessel in the ear of the rabbit within the channel. As such, at least a portion of the needle can be contained within the injection device 200 during injection or withdrawal of a substance in/from the animal (rabbit), and the individual performing the procedure can be protected from the needle.

In exemplary aspects, and with reference to FIGS. 7-13, the channel 204 can have an arcuate profile extending from the first end surface 216 to the base surface 222 of the housing. Optionally, in these aspects, the central axis 206 of the channel 204 (and the surfaces of the housing defining the channel) can have a variable radius of curvature that varies between the first end surface 216 and the base surface 222. In exemplary aspects, the end portions of the central axis 206 proximate the first end surface 216 and the base surface 222 can have a greater radius of curvature than the intermediate portions of the central axis positioned between the end portions. As further disclosed herein, it is contemplated that within the end portions, the central axis 206 can be substantially parallel to the first or second injection axes 210, 214 or be angled relative to the first or second injection axes at a selected acute angle. Alternatively, in other aspects, the central axis 206 of the channel 204 (and the surfaces of the housing defining the channel) can have a substantially consistent radius of curvature between the first end surface 216 and the base surface 222.

In one aspect, the channel 204 in the injection device 200 is at least partially open. In this aspect, and as depicted in FIGS. 7-13, it is contemplated that at least a portion of the channel 204 extending between the first end surface and the base surface is not completely enclosed by the housing. The open part of the channel 204 can be oriented relative to the third housing axis 232. Optionally, the open portion of the channel can extend radially outwardly from the central axis 206 relative to the third housing axis 232. The open portion of the channel 204 can facilitate the entry and positioning of the body part of the animal into the channel 204. For example, an ear of a rabbit can enter the channel 204 via the open portion such that the position of a vessel in the ear is relative to the first injection guide opening 208 so that a needle can penetrate the vessel when the needle enters the channel 204 via the first injection guide opening 208. In another example, an ear of a pig can enter the channel 204 via the open portion of the channel such that the position of a vessel in the ear is relative to the first injection guide opening 208 so that a needle can penetrate the vessel when the needle enters the channel 204 via the first injection guide opening 208. Thus, in operation, the ear of an animal can be positioned within the channel such that the injection axis 210 intersects a portion of a selected vessel of the ear of the animal.

Figure 12A:
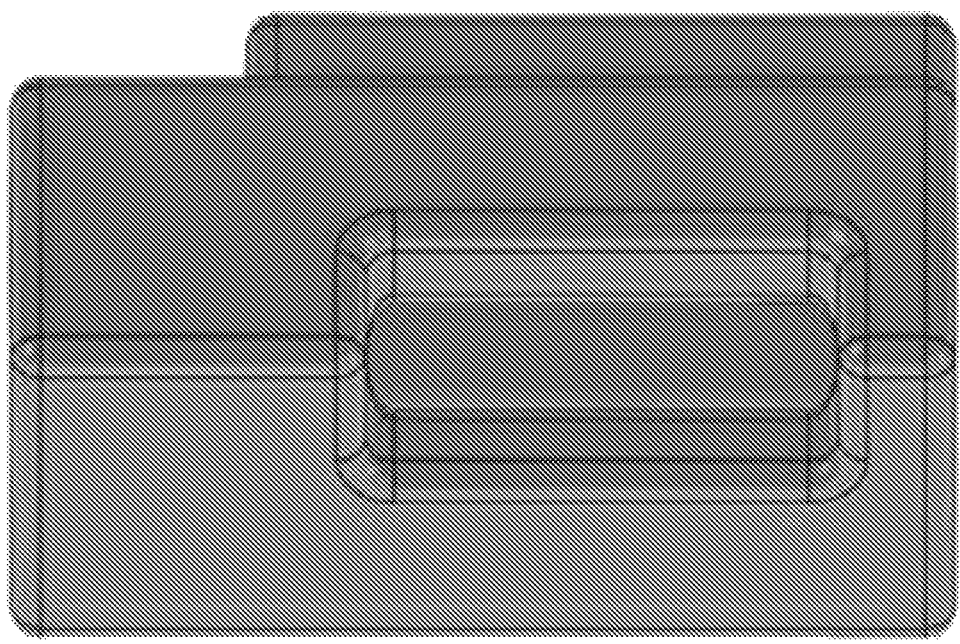
FIG. 12A shows a plan view of an exemplary injection device as disclosed herein.
Figure 12B:
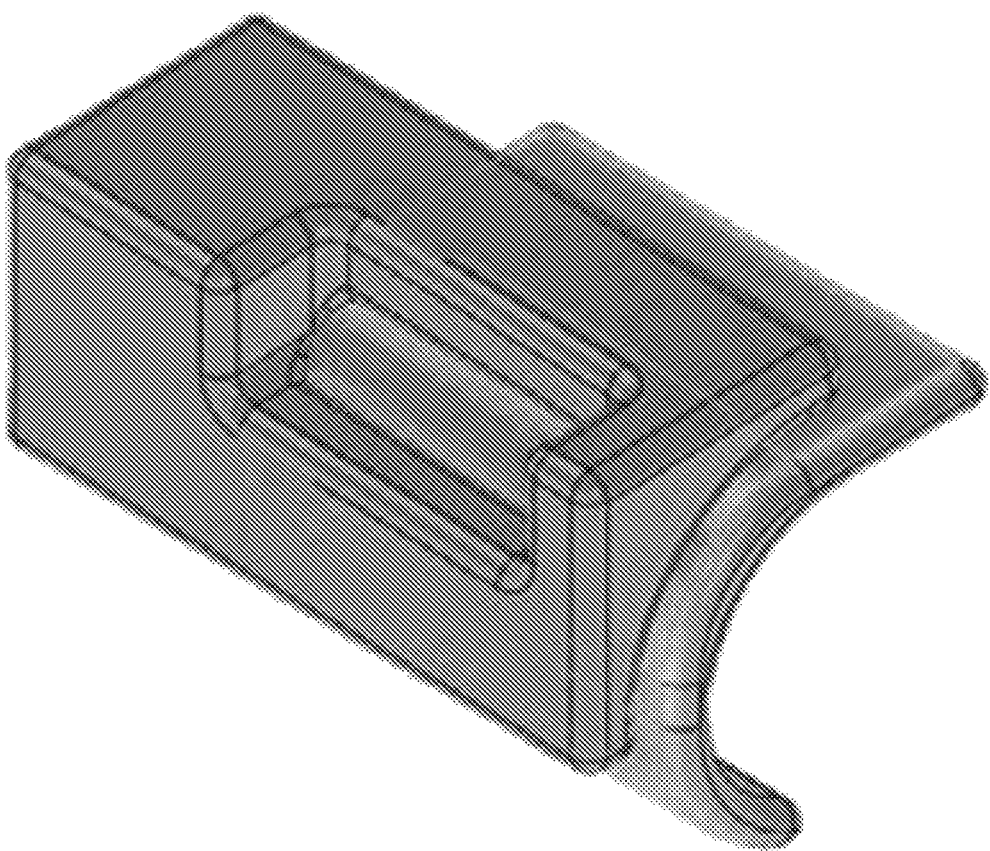
FIG. 12B shows an isometric view of the injection device of FIG. 12A.
Figure 13:
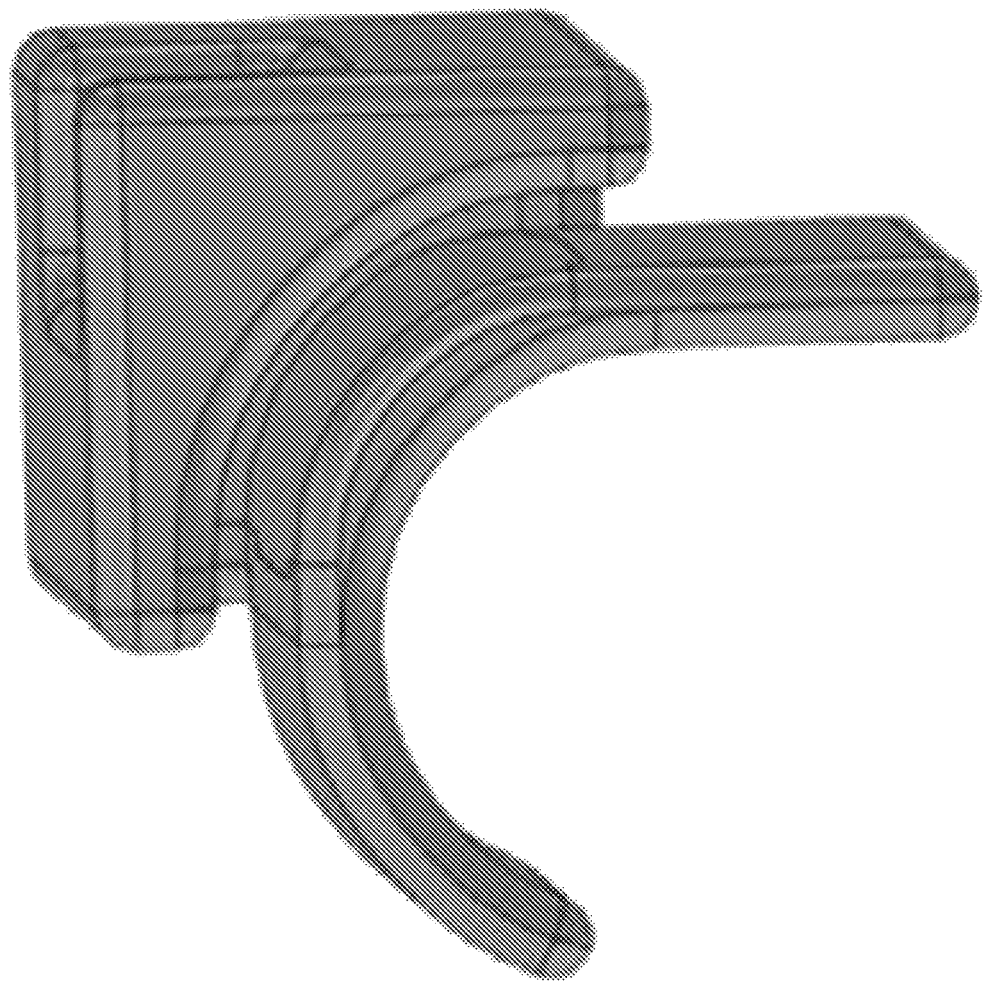
FIG. 13 shows a side perspective view of an exemplary injection device as disclosed herein.

In one aspect, the first injection guide opening 208 can be positioned such that it is located in both the first end surface 216 and one or more upper surfaces 224, see, for example, FIGS. 12A and 12B.

Figure 10A:
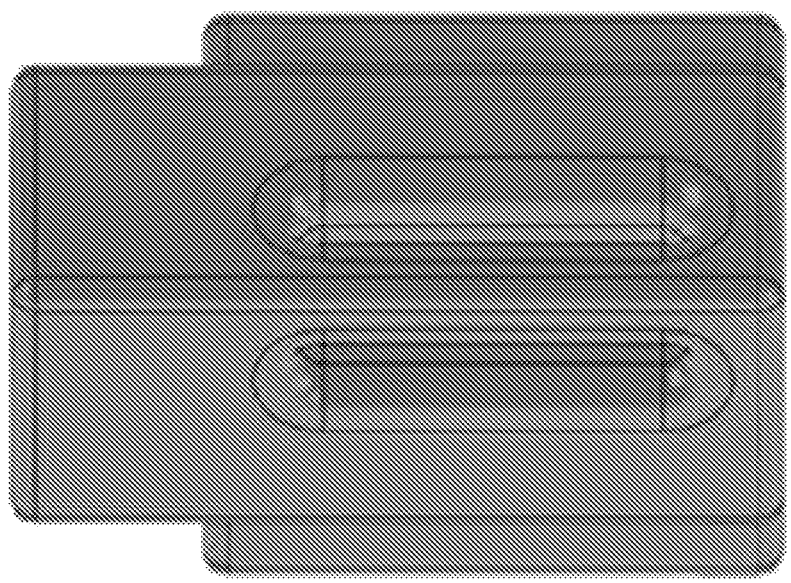
FIG. 10A shows a plan view of an exemplary injection device as disclosed herein.
Figure 10B:
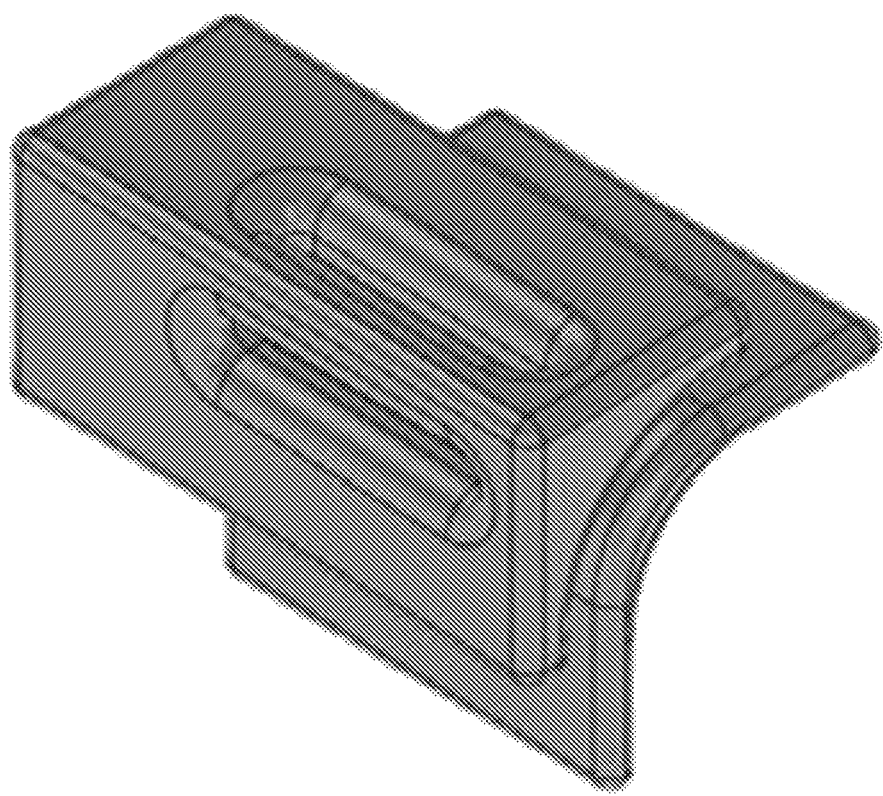
FIG. 10B shows an isometric view of the injection device of FIG. 10A.
Figure 11:
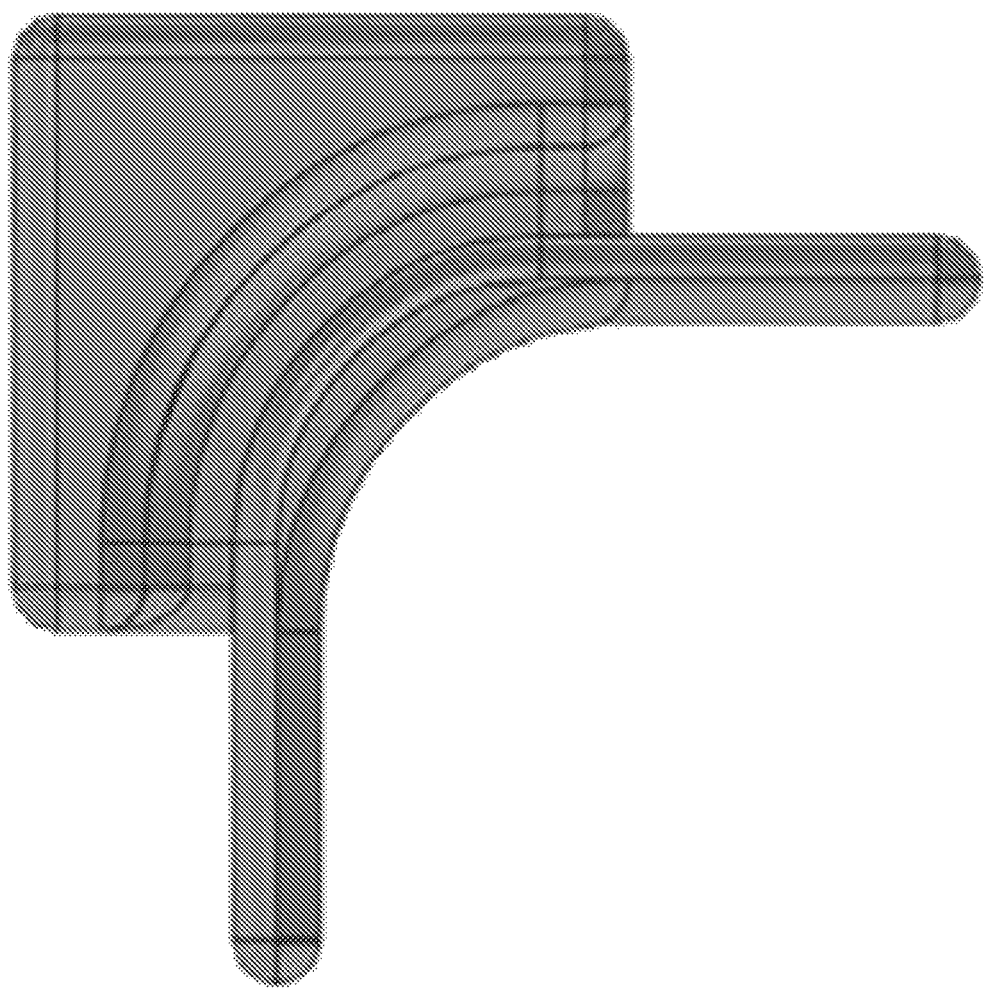
FIG. 11 shows a side view of an exemplary injection device as disclosed herein.

Similar to injection device 100, injection device 200 can also comprise a second injection guide opening, as shown in FIGS. 10A and 10B.

In one aspect, the base surface and the second end surface can be extended on one side of the channel such that the injection device 200 can be configured to fit at least one finger of an individual during use. Such a configuration is exemplified in FIGS. 10A, 10B, and 11.

In one aspect, the housing 102, 202 is made of a hard material that is resistant to needle punctures. For example, the housing 102, 202 can be made of a plastic, such as, for example, polystyrene or polycarbonate, or acrylic material.

In one aspect, at least a portion of the housing 102, 202 is transparent. For example, the housing 102, 202 can be transparent. As such, in exemplary applications, an individual can see through the injection device 100, 200 during handling to assist with positioning of the body part of the animal and the location of the needle within the injection device 100, 200. For example, the housing 102, 202 can be made of a transparent plastic, such as, for example, polystyrene or polycarbonate, or acrylic material.

In one aspect, injection device 100, 200 further comprises a heating assembly. Thus, in some aspects, the housing 102, 202 can be made of a thermally conductive material. The heating assembly can be configured to heat the body portion of an animal present in the device during use. For example, the tail of a mouse or a rat can be heated with the heating assembly, which dilates the vessel within the tail to make it easier to access with the needle. In exemplary aspects, the heating assembly can be secured, mounted, or otherwise operatively coupled to the housing at a position that permits the application of heat to a body part of an animal positioned within the channel 104, 204. It is contemplated that the heating assembly can be any conventional heating mechanism as is known in the art.

In one aspect, the injection device 100, 200 further comprises an illumination assembly. The illumination assembly can comprise a lamp or LED light that is configured to illuminate the housing 102 or 202 during use. Such a configuration provides a desired amount of illumination during usage. In exemplary aspects, the illumination assembly can be secured, mounted, or otherwise operatively coupled to the housing at a position that permits the illumination assembly to direct light within the channel 104, 204. It is contemplated that the illumination assembly can be any conventional illumination mechanism as is known in the art.

In some instances the body portion of the animal is small and it can be difficult to see the area of interest. In one aspect, the injection device 100 or 200 further comprises a magnification assembly. The magnification assembly can comprise a magnifying lens (e.g., a magnifying glass) or other magnification assembly, which assists in visually increasing the size of an object. In exemplary aspects, the magnifying assembly can be secured, mounted, or otherwise operatively coupled to the housing at a position that allows for visualization of a portion of the channel (e.g., the portion aligned with the injection guide(s)) through the magnifying assembly.

In one aspect, the first and second injection guide openings 108, 112, 208, 212 can have any cross-sectional shape. Non-limiting examples, include, circular, oval, square, rectangular, octagonal, heptagonal, hexagonal, and heptagonal. The injection guide openings 108, 112, 208, 212 can be configured to receive and fit a needle with a particular gauge. For example, the injection guide openings 108, 112, 208, 212 can be configured to receive and fit a needle with a gauge from 15 to 34, such as, for example, a gauge from 25 to 34 or a gauge from 30 to 34.

Particularly in injection device 200, the first injection guide opening 208 can be made larger than just fitting a needle. The first injection guide opening 208 can be positioned in direct alignment with the vessel being accessed, such as a vessel in a rabbit's ear. Thus, the first injection guide opening 208 can be enlarged, as shown in FIGS. 10A, 10B, 12A, 12B and 13, which enables the injection device 200 to accommodate anatomic variability. Such a configuration allows for better access to the torturous vessel, and utilization of a single device can be used on both left and right ears of a rabbit. In one aspect, the width of the first injection guide opening 208 is from 2.5 cm to about 4 cm to simultaneously provide access the vessels of the ear and allow the individual to see the vessel. Optionally, it is contemplated that the first injection guide opening 108 and the second injection guide openings 112, 212 can have a similar design.

In one aspect, the width of the channel 204 is configured to receive an ear, for example, an ear of a rabbit or pig, within the injection device 200. In one aspect, the thickness of the channel 204 is from about 0.15 cm to about 2.0 cm, such as, from about 0.25 cm to about 0.40 cm, or from about 0.50 cm to about 2.0 cm, or from about 0.50 cm to about 1.0 cm.

Figure 14:
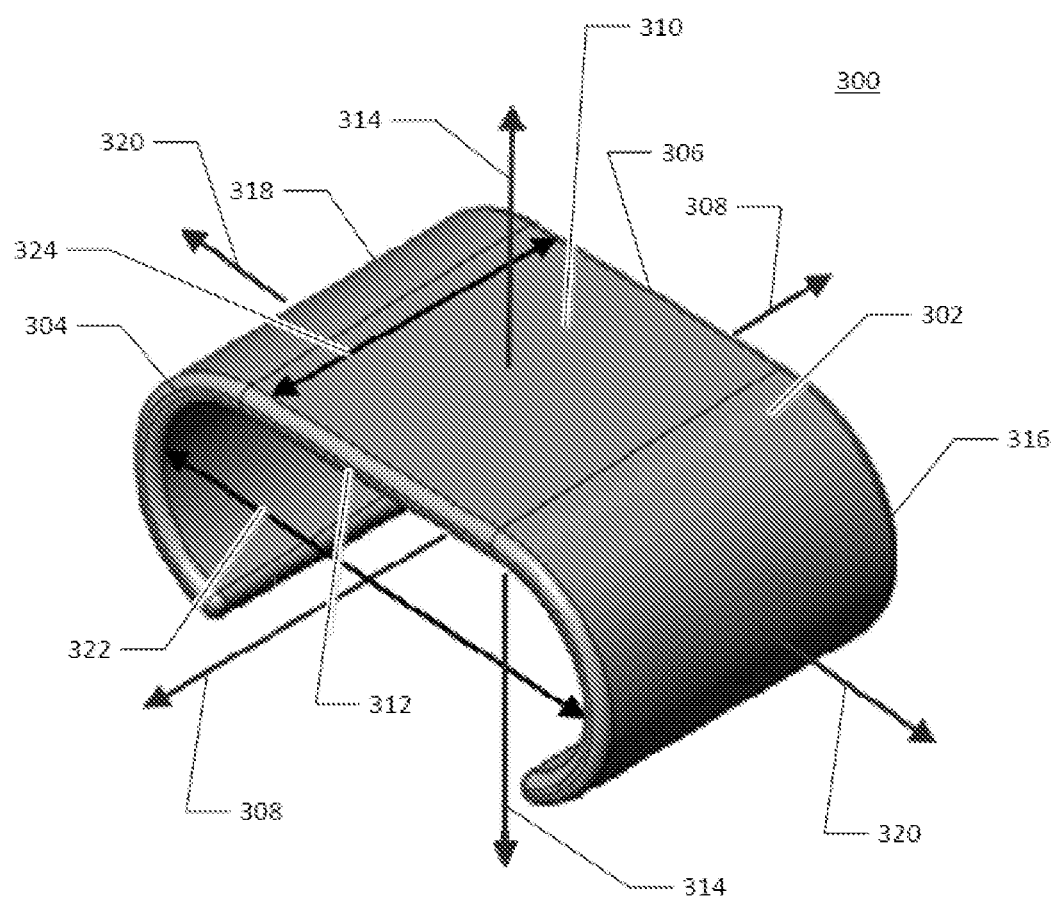
FIG. 14 shows an isometric view of an exemplary injection device as disclosed herein.
Figure 15:
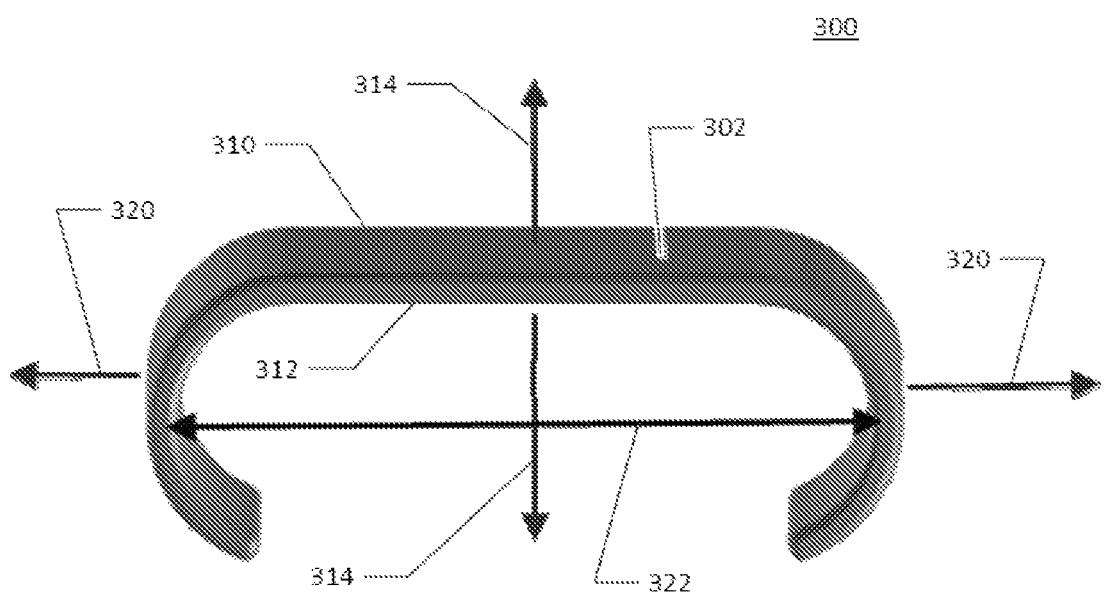
FIG. 15 shows a side view of an exemplary injection device as disclosed herein.
Figure 16:
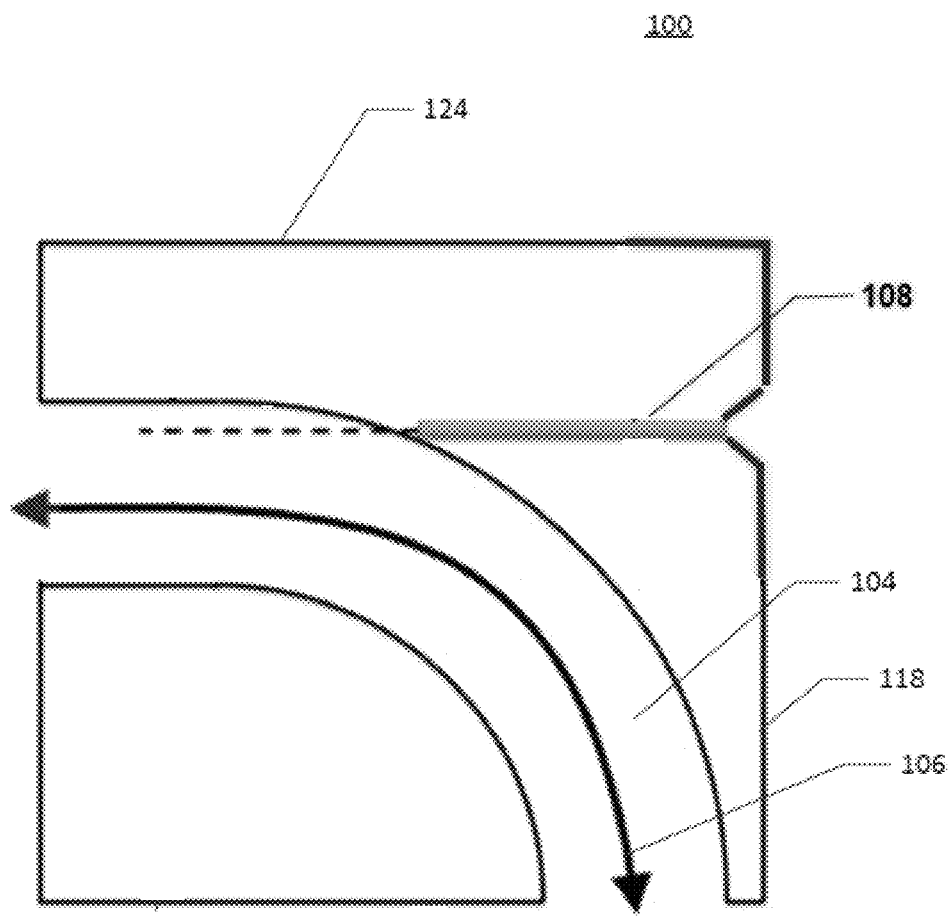
FIG. 16 shows a sectional view of an exemplary injection device as disclosed herein.

Also disclosed herein, with reference to FIGS. 14-15, is an injection device 300. The injection device 300 comprises an injection plate 302 having first and second end portions that are spaced apart relative to a first axis 320. The first and second end portions can define respective first and second side surfaces 316, 318 of the injection plate 302. The injection plate 302 can have third and fourth side surfaces 304, 306 that extend between the first and second side surfaces 316, 318 relative to the first axis 320 and are spaced apart relative to a second axis 308 that is perpendicular to the first axis 320. The injection plate 302 can have an outer surface 310 and an opposing inner surface 312 that extend between the first, second, third, and fourth side surfaces 316, 318, 304, 306 of the injection plate 302. In exemplary aspects, the first and second end portions of the injection plate 302 have respective concave inward curvatures relative to the second axis 308. In these aspects, the concave inward curvatures of the first and second end portions can be substantially complementary to a shape of at least one human finger. At least a portion of the upper surface 310 can be configured to receive and support at least a portion of an ear of an animal. Optionally, the distance between the first side surface and the second surface relative to the first axis 320 is from about 2 cm to about 10 cm. Optionally, the distance between the third side surface 304 and the fourth side surface 306 relative to the second axis 308 is from about 3 cm to about 7 cm.

In one aspect, the distance between the first side surface 316 and the second surface 318 relative to the first axis 320 is from about 1 cm to about 10 cm. In another aspect, the distance between the first side surface 316 and the second surface 318 relative to the first axis 320 is from about 3 cm to about 10 cm. In another aspect, the distance between the first side surface 316 and the second surface 318 relative to the first axis 320 is from about 5 cm to about 10 cm. In another aspect, the distance between the first side surface 316 and the second surface 318 relative to the first axis 320 is from about 6 cm to about 10 cm. In another aspect, the distance between the first side surface 316 and the second surface 318 relative to the first axis 320 is from about 7 cm to about 10 cm. In another aspect, the distance between the first side surface 316 and the second surface 318 relative to the first axis 320 is from about 8 cm to about 10 cm.

In one aspect, the distance between the third side surface 304 and the fourth side surface 306 relative to the second axis 308 is from about 1.5 cm to about 7 cm. In another aspect, the distance between the third side surface 304 and the fourth side surface 306 relative to the second axis 308 is from about 2.5 cm to about 4.5 cm.

The form of the injection plate 302 can be configured to fit a portion of from 1 to 4 fingers of an individual working with the injection device 300. In one aspect, the injection plate 302 is configured to fit one finger of an individual working with the injection device 300. In another aspect, the injection plate 302 is configured to fit two fingers of an individual working with the injection device 300. In yet another aspect, the injection plate 302 is configured to fit three fingers of an individual working with the injection device 300. In yet another aspect, the injection plate 302 is configured to fit four fingers of an individual working with the injection device 300.

In one aspect, the injection plate 302 is made of a material that is resistant to needle puncture. For example, the injection plate 302 can be made of a plastic, such as, for example, polystyrene or polycarbonate, or acrylic material.

In one aspect, at least a portion of the injection plate 302 is transparent. For example, substantially the entire injection plate 302 can be transparent. For example, the injection plate 302 can be made of a transparent plastic, such as, for example, polystyrene or polycarbonate, or acrylic material. As such, an individual can see the through the injection plate 302 during handling to assist in the positioning of the body part of the animal and visualization of the location of the injection plate 302 with respect to the fingers of the individual.

In one aspect, injection device 300 further comprises a heating assembly. Thus, in some aspects, the injection plate 302 can be made of a thermally conductive material. The heating assembly can be configured to heat the body portion of an animal present in the device during use. For example, the earl of a rabbit can be heated with the heating assembly, which enlarges the vessel within the ear to make it easier to access with the needle. In exemplary aspects, the heating assembly can be secured, mounted, or otherwise operatively coupled to the injection plate 302 at a position that permits the application of heat to a body part of an animal supported by the injection plate. It is contemplated that the heating assembly can be any conventional heating mechanism as is known in the art.

In one aspect, the injection device 300 further comprises an illumination assembly. The illumination assembly can comprise a lamp or LED light that is configured to illuminate the injection plate 302 during use. Such a configuration provides a desired amount of illumination during usage. In exemplary aspects, the illumination assembly can be secured, mounted, or otherwise operatively coupled to the injection plate 302 at a position that permits the illumination assembly to direct light toward the portion of the injection plate that supports a body part of an animal. It is contemplated that the illumination assembly can be any conventional illumination mechanism as is known in the art.

In some instances the body portion of the animal is small and it can be difficult to see the area of interest. In one aspect, the injection device 300 further comprises a magnification assembly. The magnification assembly can comprise a magnifying glass, which assists in visually increasing the size of an object. In exemplary aspects, the magnifying assembly can be secured, mounted, or otherwise operatively coupled to the injection plate 302 at a position that allows for visualization of a portion of the injection plate through the magnifying assembly.

The injection devices 100, 200, 300 disclosed herein can be configured to receive a portion of a body part of an animal selected from the group consisting of rodent, including rat or mouse, rabbit, pig, dog, and goats.

The injection devices 100, 200, 300 disclosed herein can be a reusable device and, thus, be made with a material than can easily be cleaned and/or sterilized between uses by the end user.

In one aspect, the injection device disclosed herein can be a disposable injection device. A disposable injection device can be configured and made from materials suitable for being used only once. A disposable injection device should not be used more than once.

2. METHOD

Also disclosed herein are methods of using the devices disclosed herein.

Disclosed is a method comprising a) providing the injection device disclosed herein; b) placing a body portion of an animal in the channel; and c) administering a substance to or withdrawing a fluid from a vessel in the body portion of the animal via a needle placed through the first injection guide opening.

In one aspect, the injection device is the injection device 100 disclosed herein. In another aspect, the injection device is the injection device 200 disclosed herein.

In one aspect, the body portion is a tail, and wherein the animal is a mouse or rat. In another aspect, the body portion is an ear, and wherein the animal is a rabbit or pig.

The method disclosed herein can be performed by one or more individuals. For example, the method disclosed herein can be performed by one individual. The method disclosed herein protects a user from accidentally sticking themselves with the needle. Thus, in one aspect, the administration of the substance to or the withdrawal of the fluid from the vessel is performed within the channel of the injection device.

Also disclosed herein is a method comprising a) providing the injection device with an injection plate disclosed herein; b) placing at least one finger between the first and second end and against the inner surface of the injection plate;

placing a body portion of an animal on the outer surface of the injection plate; and administering a substance to or withdrawing a fluid from a vessel in the animal.

In one aspect, the injection device comprising an injection plate is the injection device 300 disclosed herein.

In one aspect, step b) comprises placing at least one finger between the first and second end and against the inner surface of the injection plate. In another aspect, step b) comprises placing at least two fingers between the first and second end and against the inner surface of the injection plate. In another aspect, step b) comprises placing at least three fingers between the first and second end and against the inner surface of the injection plate. In yet another aspect, step b) comprises placing four fingers between the first and second end and against the inner surface of the injection plate.

In one aspect, the body portion is an ear, and wherein the animal is a rabbit or pig. For example, the animal can be a rabbit.

3. EXAMPLES

Mice are commonly used to model many diseases due to cost effectiveness, easy maintenance, rapid reproduction, etc. The tail vein is a common route to deliver agents intravenously, but inserting a needle into tail vein is very challenging; the diameter of mouse tail vein is around 0.5 mm, slightly larger than the diameter of a 30 G needle (0.3 mm), so even highly trained technicians experience 10~20% failure. It is also not uncommon that technicians come in contact with the needle tip during the procedure and can in some instances puncture their own skin with the needle.

Technicians have a difficult time inserting the needle parallel to the vein in the mouse-tail, which can lead to that the injection is not successful. For example, if a needle is inserted with an angle, it can easily break through the vein.

Figure 5A:
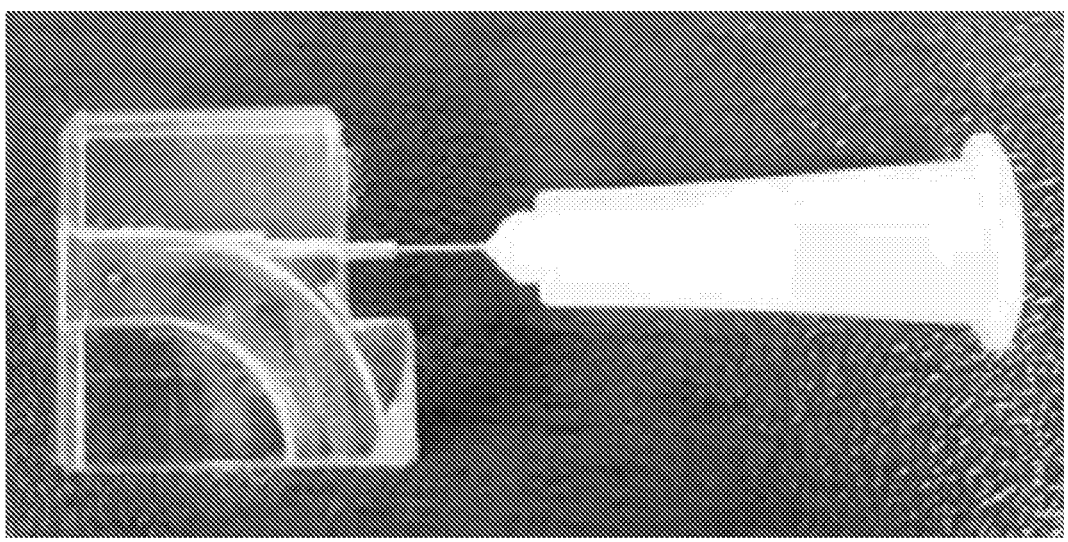
FIGS. 5A and 5B show photographs of an exemplary injection device as disclosed herein.
Figure 5B:
Figure 6A:
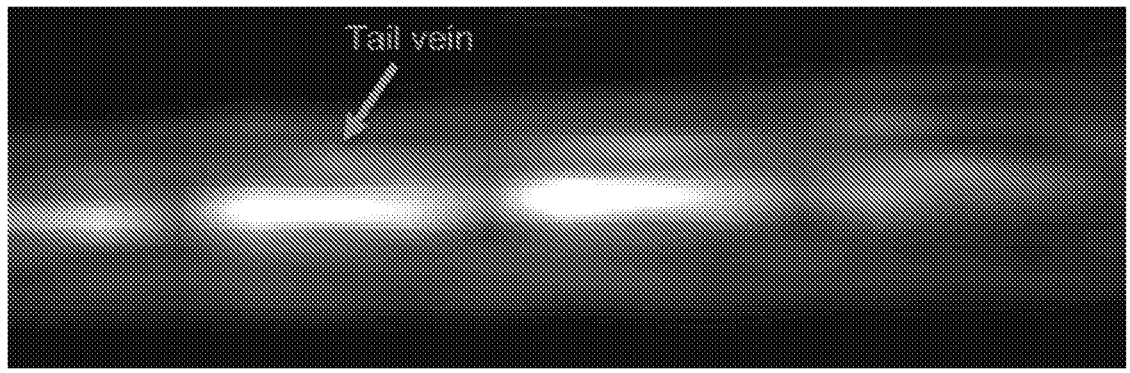
FIGS. 6A and 6B show magnetic resonance images of a mouse-tail indicating the tail vein within the mouse-tail.
Figure 6B:
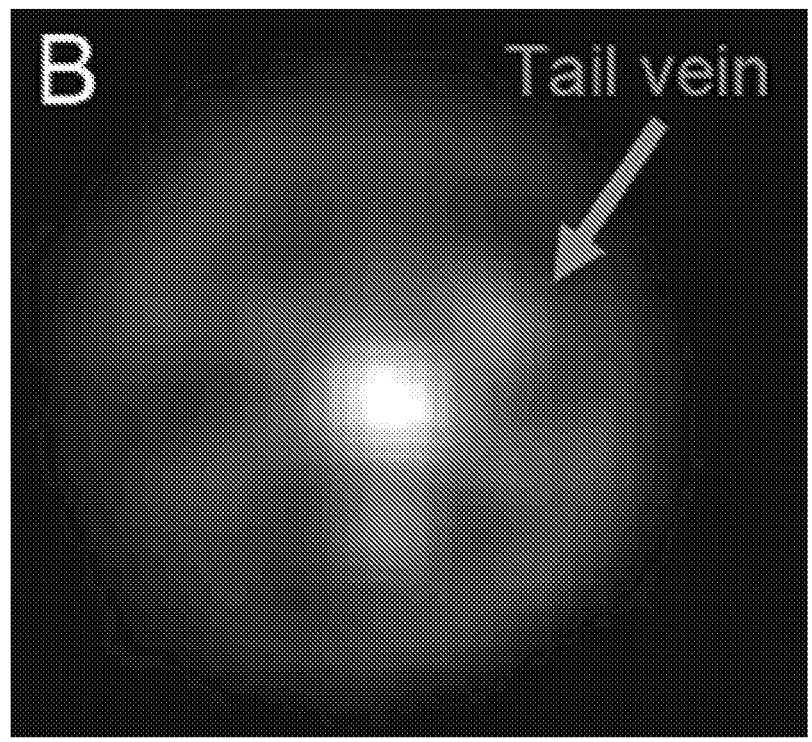
Figure 7:
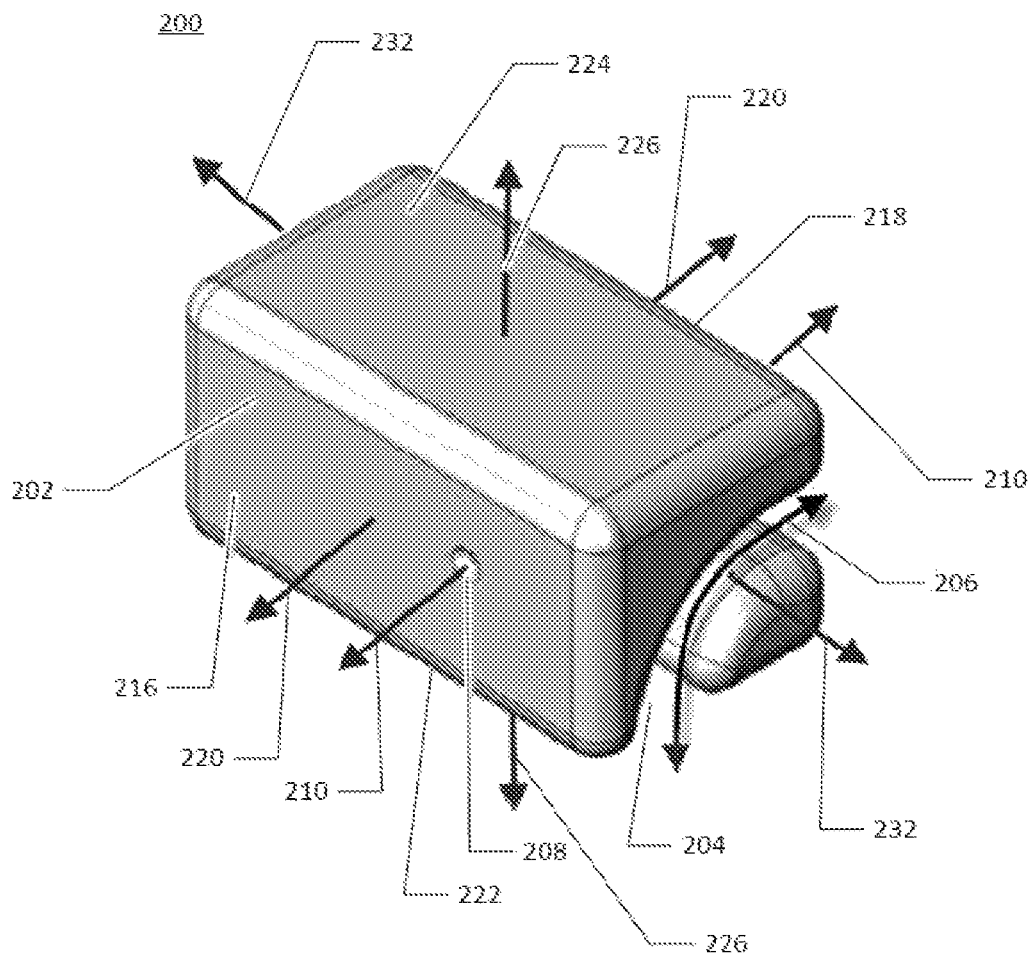
FIG. 7 shows a front isometric view of an exemplary injection device as disclosed herein.
Figure 8:
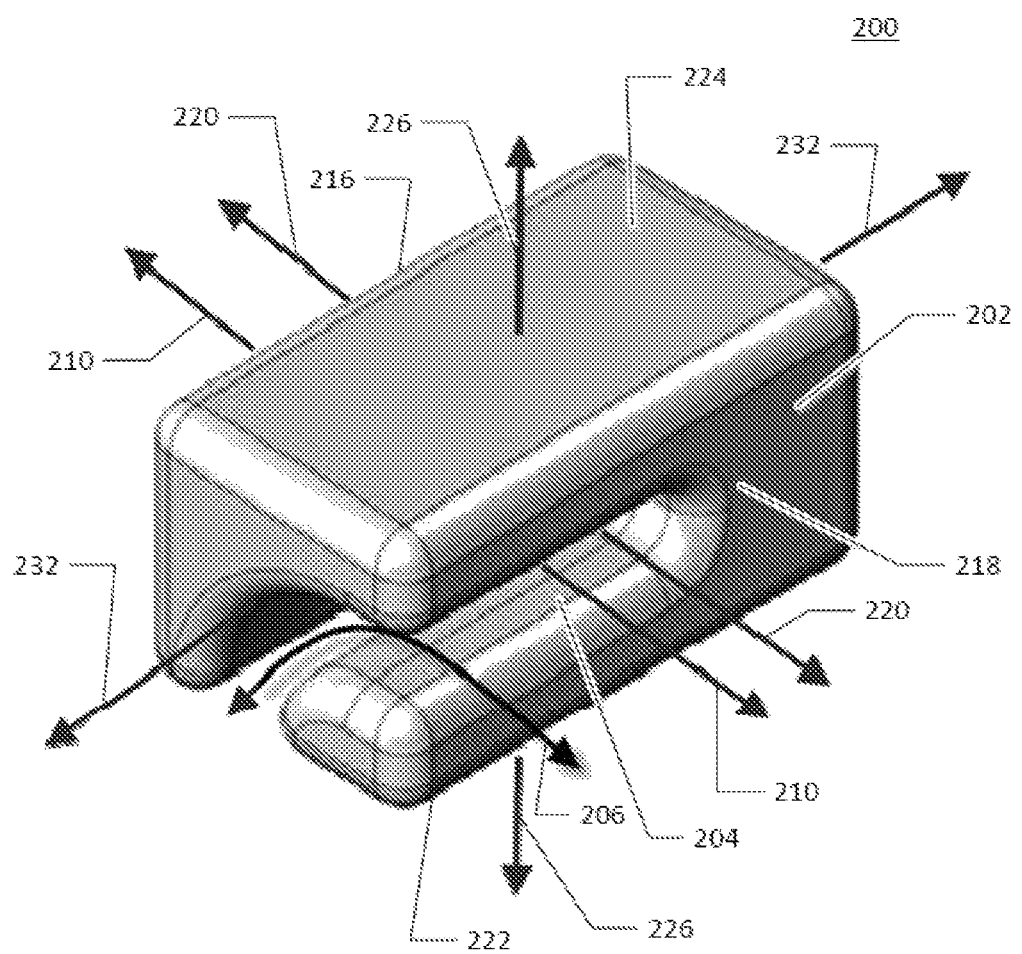
FIG. 8 shows a back isometric view of an exemplary injection device as disclosed herein.
Figure 9A:
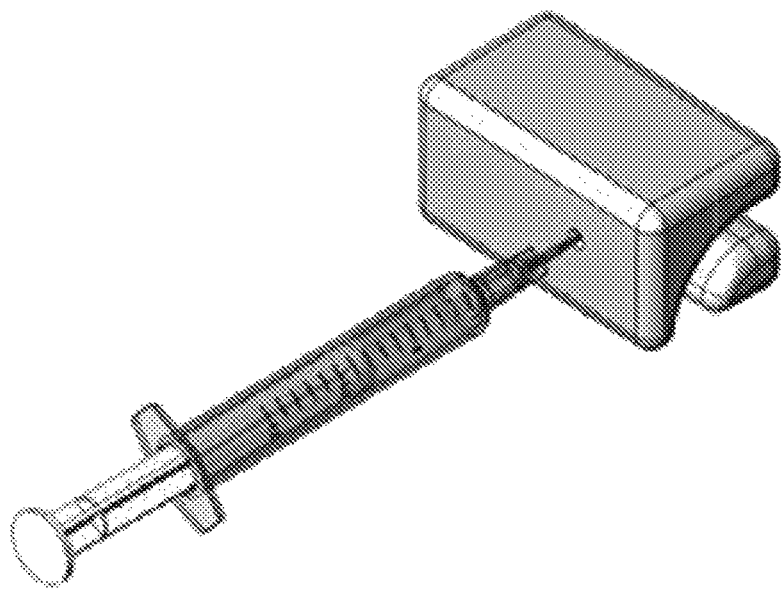
FIG. 9A shows a front isometric view of an exemplary injection device as disclosed herein.
Figure 9B:
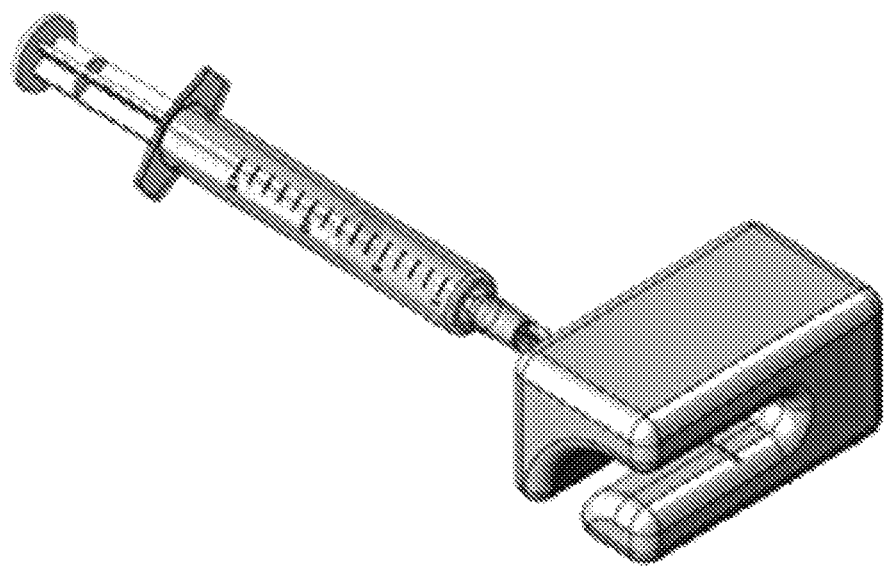
FIG. 9B shows a back isometric view of the injection device of FIG. 9A.

The injection device shown in FIGS. 5A and 5B was used to inject a substance into a mouse tail-vein. The injection device shown in FIGS. 5A and 5B has a size of 10×15×15 mm and made of plastic. The depth of the tail vein of six nude mice (25~35 g) were measured using MRI (magnetic resonance imaging), see FIGS. 6A and 6B. FIGS. 6A and 6B show MR images of a tail of a representative nude mouse, when the mouse temperature was regulated to 37° C. It was found that the center of tail vein is located at 0.67±0.04 mm (mean±SD) under the surface. The injection device shown in FIGS. 5A and 5B were used to guide a 30 G needle to 0.65 mm under the surface in parallel to the tail vein. Multiple injections were made at a success rate of 100%, that is, the tail-vein was penetrated every time an injection was attempted. Furthermore, the individual performing the experiment was protected from the needle during the procedure by the injection device.

What is claimed is:

1. An injection device comprising
   a) a housing defining an arcuate channel and a first injection guide opening, the arcuate channel having a central axis, the first injection guide opening surrounding a first injection axis, wherein the first injection guide opening extends linearly to the arcuate channel, wherein the housing comprises
      i) first and second end surfaces that are spaced apart relative to a first housing axis;
      ii) a base surface extending between the first and second end surfaces; and
      iii) at least one upper surface extending between the first and second end surfaces, wherein the base surface and the at least one upper surface are spaced apart relative to a second housing axis that is perpendicular to the first housing axis;
   wherein the arcuate channel of the housing extends from the first end surface to the base surface,
      wherein the first injection guide opening is positioned in fluid communication with the arcuate channel, and
      wherein the first injection axis is substantially parallel to the first housing axis or the second housing axis.

2. The injection device of claim 1, wherein the housing further defines a second injection guide opening surrounding a second injection axis, wherein the second injection guide opening is positioned in fluid communication with the arcuate channel, and wherein the second injection axis is substantially parallel to the first housing axis or the second housing axis.

3. The injection device of claim 2, wherein the first injection guide opening extends from an upper surface of the at least one upper surface to the arcuate channel, wherein the first injection axis is substantially parallel to the first housing axis, wherein the second injection guide opening extends from an upper surface of the at least one upper surface to the arcuate channel, and wherein the second injection axis is substantially parallel to the second housing axis.

4. The injection device of claim 2, wherein at least a portion of the central axis of the arcuate channel is substantially parallel to the second injection axis.

5. The injection device of claim 4, wherein the at least a portion of the central axis that is substantially parallel to the second injection axis is spaced apart from the second injection axis relative to the second housing axis at a distance from about 0.8 mm to about 1.4 mm.

6. The injection device of claim 2, further comprising a first injection insert guide that is at least partially received within the first injection guide opening, wherein the first injection insert guide surrounds the first injection axis.

7. The injection device of claim 2, further comprising a second injection insert guide that is at least partially received within the second injection guide opening, wherein the second injection insert guide surrounds the second injection axis.

8. The injection device of claim 1, wherein the first injection guide opening extends from an upper surface of the at least one upper surface to the arcuate channel, and wherein the first injection axis is substantially parallel to the first housing axis.

9. The injection device of claim 1, wherein the first injection guide opening extends from an upper surface of the at least one upper surface to the arcuate channel, and wherein the first injection axis is substantially parallel to the second housing axis.

10. The injection device of claim 1, wherein the first injection guide opening extends from the second end surface to the arcuate channel, and wherein the first injection axis is substantially parallel to the first housing axis.

11. The injection device of claim 1, wherein at least a portion of the central axis of the arcuate channel is substantially parallel to the first housing axis.

12. The injection device of claim 1, wherein the arcuate channel has a width from about 2 mm to about 5 mm.

13. The injection device of claim 1, wherein at least a portion of the central axis of the arcuate channel is substantially parallel to the first injection axis.

14. The injection device of claim 13, wherein the at least a portion of the central axis that is substantially parallel to the first injection axis is spaced apart from the first injection axis relative to the first housing axis at a distance from about 0.8 mm to about 1.4 mm.

15. The injection device of claim 1, wherein the arcuate channel is an enclosed arcuate channel.

16. The injection device of claim 15, wherein the enclosed arcuate channel is configured to receive at least a portion of a tail of a rodent.

17. The injection device of claim 1, wherein the arcuate channel is at least partially open.

18. A method comprising
  a) providing the injection device of claim 1;
  b) placing a body portion of an animal in the arcuate channel; and
  c) administering a substance to or withdrawing a fluid from a vessel in the body portion of the animal via a needle placed through the first injection guide opening.

* * * * *